(12) United States Patent
Kahlman (10) Patent No.: US 10,524,955 B2
(45) Date of Patent: Jan. 7, 2020

(54) SYSTEM AND METHOD FOR CONTROLLING A TEMPERATURE

(71) Applicant: KONINKLIJKE PHILIPS N.V., Eindhoven (NL)

(72) Inventor: Josephus Arnoldus Henricus Maria Kahlman, Tilburg (NL)

(73) Assignee: Koninklijke Philips N.V., Eindhoven (NL)

( * ) Notice: Subject to any disclaimer, the term of this patent is extended or adjusted under 35 U.S.C. 154(b) by 244 days.

(21) Appl. No.: 15/520,445

(22) PCT Filed: Oct. 28, 2015

(86) PCT No.: PCT/EP2015/074999
§ 371 (c)(1),
(2) Date: Apr. 20, 2017

(87) PCT Pub. No.: WO2016/066693
PCT Pub. Date: May 6, 2016

(65) Prior Publication Data
US 2017/0312120 A1    Nov. 2, 2017

(30) Foreign Application Priority Data

Oct. 29, 2014  (EP) .................................... 14190904

(51) Int. Cl.
*H05B 1/02* (2006.01)
*A61F 7/00* (2006.01)
*A61B 5/1455* (2006.01)

(52) U.S. Cl.
CPC .......... *A61F 7/007* (2013.01); *A61B 5/14551* (2013.01); *H05B 1/025* (2013.01);
(Continued)

(58) Field of Classification Search
CPC ...... A61F 2007/0071; A61F 2007/0074; A61F 2007/0095; A61B 5/14551; H05B 1/02; H05B 2203/035; H05B 3/0085
(Continued)

(56) References Cited

U.S. PATENT DOCUMENTS 4,278,870 A    7/1981  Carleton et al.
4,290,431 A    9/1981  Herbert et al.
(Continued)

FOREIGN PATENT DOCUMENTS

DE        3406966 A1    8/1985
JP      H05293180 A   11/1993
(Continued)

*Primary Examiner* — Mark H Paschall
(74) *Attorney, Agent, or Firm* — Michael W. Haas (57) ABSTRACT

The present invention relates to a system (100) for controlling a temperature, the system (100) comprising: a temperature sensor module (10), which is configured to measure a temperature value; a microcontroller module (20), which is coupled to the temperature sensor module (10) and which is configured to generate AC heating pulse signals by separate sequential code steps based on the measured temperature value; a coupling module (30) which is coupled to the microcontroller module (20) and which is configured to transform the generated AC heating pulse signals into transformed AC heating pulse signals using a transfer function which is substantially zero for DC signal components; and a heating module (40) which is coupled to the coupling module (30) and which is configured to generate heat according to the transformed AC heating pulse signals.

18 Claims, 6 Drawing Sheets

(52) U.S. Cl.
CPC ............... *A61F 2007/0071* (2013.01); *A61F 2007/0095* (2013.01)

(58) Field of Classification Search
USPC .............................. 219/497, 492, 494, 501
See application file for complete search history.

(56) References Cited

U.S. PATENT DOCUMENTS

| | | | | |
|---|---|---|---|---|
| 4,296,752 | A | | 10/1981 | Welsh et al. |
| 5,425,868 | A | | 6/1995 | Pedersen |
| 5,789,723 | A | * | 8/1998 | Hirst ................ G03G 15/80 219/216 |
| 5,793,022 | A | * | 8/1998 | Klinck ............... G05B 13/024 219/121.43 |
| 5,811,764 | A | * | 9/1998 | Hirst ................ G03G 15/2003 219/485 |
| 7,613,855 | B2 | * | 11/2009 | Phillips ............... F24H 9/2021 710/2 |
| 9,354,122 | B2 | * | 5/2016 | Bieberich ............ G01K 1/165 |
| 9,690,362 | B2 | * | 6/2017 | Leimbach ............ A61B 17/068 |
| 2005/0082276 | A1 | * | 4/2005 | Hirst ................ G03G 15/2039 219/492 |
| 2008/0262334 | A1 | | 10/2008 | Dunn |
| 2009/0143725 | A1 | | 6/2009 | Peyser |
| 2010/0312314 | A1 | | 12/2010 | Ice et al. |
| 2011/0202019 | A1 | | 8/2011 | Cooper et al. |
| 2012/0157804 | A1 | | 6/2012 | Rogers |
| 2014/0143064 | A1 | | 5/2014 | Tran |

FOREIGN PATENT DOCUMENTS

| | | |
|---|---|---|
| JP | H07507955 A | 9/1995 |
| JP | H11168830 A | 6/1999 |
| JP | 2003305075 A | 10/2003 |
| JP | 2010113992 A | 5/2010 |
| RU | 2011150407 A | 6/2013 |
| RU | 2013108550 A | 9/2014 |
| WO | 9105300 A1 | 4/1991 |
| WO | 2006063202 A2 | 6/2006 |
| WO | WO2010053011 A1 | 5/2010 |

* cited by examiner

SYSTEM AND METHOD FOR CONTROLLING A TEMPERATURE

CROSS-REFERENCE TO PRIOR APPLICATIONS

This application is the U.S. National Phase application under 35 U.S.C. § 371 of International Application No. PCT/EP2015/074999, filed on Oct. 28, 2015, which claims the benefit of European Patent Application No. 14190904.4, filed on Oct. 29, 2014. These applications are hereby incorporated by reference herein.

FIELD OF THE INVENTION

The present invention relates to the field of miniaturized controller for skin heating. In particular, the present invention relates to a system and a method for controlling a temperature.

BACKGROUND OF THE INVENTION

Neuromuscular disease, COPD and obese hyperventilation patients often suffer from chronic respiratory failure. Said patients need regular treatment of their respiratory failure at home. Hypoxemic patients are treated by oxygen therapy, mostly without ventilator support, while treatment by non-invasive ventilation with environmental air helps bringing the high carbon dioxide blood gas level of hypercapnic patients back to an acceptable level. The efficiency of the ventilation is checked by measuring the baseline and the trends in arterial oxygen and carbon dioxide levels during nocturnal NIV.

Transcutaneous $CO_2$ sensors are used at home instead of arterial blood gas analysis. Arterial blood gas analysis is widely used, but needs sample taking by a professional, is painful and can have complications. Transcutaneous $CO_2$ sensors are accepted for domiciliary care, and also in the hospital for $CO_2$ monitoring.

To derive the transcutaneous $CO_2$ value from the measured—cutaneous—partial $CO_2$ pressure, the difference between the sensor temperature and the arterial blood temperature of 37° C. has to be taken into account. Furthermore, an offset is subtracted from the measured value to compensate for the skin metabolism that varies somewhat with skin temperature.

Arterialization of the skin is essential for transcutaneous blood gas measurements to obtain a transcutaneous value that reflects the arterial $CO_2$ blood gas level. Existing technology is based on arterialization by heating the skin below the sensor surface. In currently available transcutaneous systems the minimal sensor temperature for stable arterialization is 42° C. and the required heating power is ~500 mW at maximum, which is mainly needed to compensate for the cooling effect of the blood flow.

The prevention of skin-burns is a main concern in skin heating. As the heater is DC coupled, electronic failures in e.g. the driver circuitry or software errors may lead to uncontrollable heater currents. To safe-guard such situations a substantial amount of hardware is added to the main temperature control loop.

Chemo optical sensor materials may be applied to measure $CO_2$ transcutaneously. Chemo optical sensor may comprise the following: On top of an optical transparent carrier material two layers of 'silicon rubber-like' gas-permeable materials are deposited. The first layer—the sensing layer— comprises a mixture of two fluorescent dyes in chemical buffer material; namely a reference dye having a long fluorescent life-time and a pH-sensitive indicator dye having a short life-time. The second layer—the membrane—comprises light reflecting material ($TiO_2$) particles and prevents ion transport to and from the sensing layer. $CO_2$ gas diffuses through said membrane into the first layer and changes the pH, which change the fluorescence from the indicator dye. By a dual life-time referencing technique, effectively measuring the time response to modulated light excitation, the percentage $CO_2$ gas is calculated. At first sight the properties of these sensor spots look unmistakeable advantageous for the design of a disposable transcutaneous sensor device for the home market in terms of: dynamic range, pre-calibration, compensation for deviating temperature, stability, and cost-effectiveness.

Skin heating and contact fluid are essential to achieve sufficient and stable skin arterialization. For this purpose the sensor temperature must be accurately controlled in a range between 40~45° C. In the ideal situation the foreseen nocturnal transcutaneous $CO_2$ monitor system is wear-able, preferably cable-less and has a small form factor.

SUMMARY OF THE INVENTION

There may be a need to improve miniaturized, inherent-safe controller for skin heating as well as devices and methods for controlling the temperature.

These needs are met by the subject-matter of the independent claims. Further exemplary embodiments are evident from the dependent claims and the following description. An aspect of the present invention relates to a system for controlling a temperature, the system comprising: a temperature sensor module, which is configured to measure a temperature value; a microcontroller module, which is coupled to the temperature sensor module and which is configured to generate AC heating pulse signals by separate sequential code steps based on the measured temperature value; a coupling module, which is coupled to the microcontroller module and which is configured to transform the generated AC heating pulse signals into transformed AC heating pulse signals using a transfer function which is substantially zero for DC signal components; and a heating module, which is coupled to the coupling module and which is configured to generate heat according to the transformed AC heating pulse signals.

The microcontroller module is configured to generate AC heating pulse signals by separate sequential code steps, in other words, basically the generated output power after AC coupling is modulated by duty cycle-per-heating pulse, duty cycle-per-thermal control-loop cycle (the number of heating pulses) or frequency.

The present invention advantageously provides a system for thermostatically controlling a temperature. The present invention advantageously provides a controlling of a dissipative heating element via coupling means, wherein AC current can flow through the coupling means.

The present invention may be not limited to transcutaneous sensing only, but can be extended to any controller for a dissipative element in healthcare and beyond. Examples are: ablation catheters, electronic heat patches, zero-heat flux temperature sensors for measuring e.g. body core temperature, exposure control for light applications, controllers for mechanical actuators like positioning servo's etc.

In other words: The present invention advantageously restricts that energy packets or heating pulses generated by distinct code steps can generate heat or energy, in case of a mechanical actuator. The present invention advantageously uses software modules which are operated in a serial or sequential way. In other words, no parallel processing or multicore processors or hard-wired pulse generators are used in order to guarantee that any hang-up will stop the generation of heating pulses.

The present invention advantageously provides an increased safety level, because any software issue will result in less power output due to the fact that only current fluctuations or heating pulses are able to generate heat. Because every single heating pulse requires the execution of distinct code steps, instead of simply controlling a hard-wired pulse-width or frequency modulator, software hang-ups will not cause any harm.

The transcutaneous $CO_2$ sensor module may comprise two parts: a disposable plaster comprising the chemo optical sensor material. The second part comprises the optical read-out and the temperature control system. Optionally the heating module may be part of the disposable (plaster), AC coupled (capacitive/inductive) to the non-disposable part.

The term AC or DC as used by the present invention may refer to alternating current (AC, also ac) or direct current (DC, also dc), respectively. In the case of AC, the flow of electric charge periodically reverses direction. In direct current, the flow of electric charge is only in one direction. The abbreviations AC and DC are often used to mean simply alternating and direct, as when they modify current or voltage.

The present invention advantageously allows adapting to any DC offsets generated by a driver circuit, for instance generated due to component failures.

The present invention advantageously allows achieving additional safety by software detection of hardware bucks, such as ADC failure, system clock failure, or temperature sensor shorting or any other failure.

The present invention advantageously provides a miniaturization due to the minimal number of electronic components and a use of one single supply voltage.

According to a further, second aspect of the present invention, the present invention provides a medical system comprising a system according to the first implementation form or according to any embodiment of the first implementation.

According to a further, third aspect of the present invention, a method for controlling a temperature is provided, the method comprising the steps of: measuring a temperature value by means of a temperature sensor module; generating AC heating pulse signals by separate sequential code steps based on the measured temperature value by means of a microcontroller module; transforming the generated AC heating pulse signals into transformed AC heating pulse signals using a transfer function which is substantially zero for DC signal components by means of a coupling module; and generating heat according to the transformed AC heating pulse signals by means of a heating module.

The term "substantially zero for DC signal components" as used by the present invention may refer to a transfer function which is for instance lower than 0.1 or lower than 0.05 for DC components, for instance whereby DC means that a frequency of the component is lower than 1 Hz or preferably lower than 0.5 Hz or particularly preferred lower than 0.1 Hz. This advantageously allows a digital and pulsed and secure way of generating heat in quantized amounts.

According to an exemplary embodiment of the present invention, the heating module is configured to generate the heat according to the transformed AC pulse signals in form of heating pulses of a time interval between 1 μs and 500 ms, preferably between 2 μs and 30 ms, and particularly preferred between 5 μs and 100 μs. This advantageously allows a digital and pulsed and secure way of generating heat in quantized amounts.

According to an exemplary embodiment of the present invention, the microcontroller module is a multi-core or a single-core processor and is configured to be operated in sequential processing mode. In other words, code for generating the AC heating pulse signals based on the measured temperature value is executed on the microcontroller module in form of one single-core processor. This advantageously allows a safe and reliable way of operating the microcontroller avoiding system failure or system hang-ups causing unwanted energy supply.

According to an exemplary embodiment of the present invention, the coupling module is configured to attenuate the DC signal components to a value of less than 4% of an input DC signal component, preferably to a value of less than 2% of an input DC signal component, and particularly preferred to a value of less than 0.5% of an input DC signal component. This advantageously limits providing a maximum heating level via the coupling module in case of a DC erroneous situation.

According to an exemplary embodiment of the present invention, the microcontroller module is configured to generate the AC heating pulse signals based on the measured temperature value using a duty-cycle modulation.

In other words, the microcontroller module is configured to perform and conduct a duty-cycle modulation, e.g. control the temperature per heating pulse, wherein the duty cycle of each of the heating pulses is modulated.

According to an exemplary embodiment of the present invention, the microcontroller module is configured to control a number of the generated AC heating pulse signals per thermal control loop cycle adapted to a calculated amount of requested thermal energy. This advantageously allows a precise way of generating heat and controlling the amount of heat generated.

According to an exemplary embodiment of the present invention, the microcontroller module is configured to control the duty cycle of the generated AC heating pulses adapted to a calculated amount of requested thermal energy.

According to an exemplary embodiment of the present invention, the microcontroller module is configured to generate a period of time the AC heating pulse signals based on the measured temperature value using a frequency modulation.

In other words, the microcontroller module is configured to perform a frequency modulation or heating pulse period modulation. In combination with a high-pass-or band-pass coupling characteristic the dissipated power depends on the frequency of the heating pulses.

According to an exemplary embodiment of the present invention, the microcontroller module is configured to control the period time of the generated AC heating pulses adapted to a calculated amount of requested thermal energy. This advantageously allows a safe and reliable way of heat generation.

According to an exemplary embodiment of the present invention, the microcontroller module is configured to control a frequency or an amplitude of the generated AC heating pulse signals.

According to an exemplary embodiment of the present invention, the heating module is a resistive element or a resistor or any other heat generating device.

According to an exemplary embodiment of the present invention, the coupling module is a capacitor or an inductor or a transformer. This advantageously provides a safe coupling of the microprocessor module and the heating module.

According to an exemplary embodiment of the present invention, the coupling module comprises a driver circuit. This advantageously provides a safe coupling, i.e. the microprocessor module may be used to control another circuit or other component, such as a high-power transistor in order to supply the heating module.

According to an exemplary embodiment of the present invention, the driver circuit is an H-bridge circuit.

According to an exemplary embodiment of the present invention, the microcontroller module comprises an analogue input, to which the temperature sensor module is coupled to.

A computer program performing the method of the present invention may be stored on a computer-readable medium. A computer-readable medium may be a floppy disk, a hard disk, a CD, a DVD, an USB (Universal Serial Bus) storage device, a RAM (Random Access Memory), a ROM (Read Only Memory) and an EPROM (Erasable Programmable Read Only Memory). A computer-readable medium may also be a data communication network, for example the Internet, which allows downloading a program code.

The methods, systems and devices described herein may be implemented as software in a Digital Signal Processor, DSP, in a micro-controller or in any other side-processor or as hardware circuit within an application specific integrated circuit, ASIC, CPLD or FPGA.

The present invention can be implemented in digital electronic circuitry, or in computer hardware, firmware, software, or in combinations thereof, e.g. in available hardware of a device or of a medical device or in new hardware dedicated for processing the methods described herein.

A more complete appreciation of the present invention and the advantages thereof will be more clearly understood by reference to the following schematic drawings, which are not to scale, wherein:

DETAILED DESCRIPTION OF EMBODIMENTS

Figure 1:
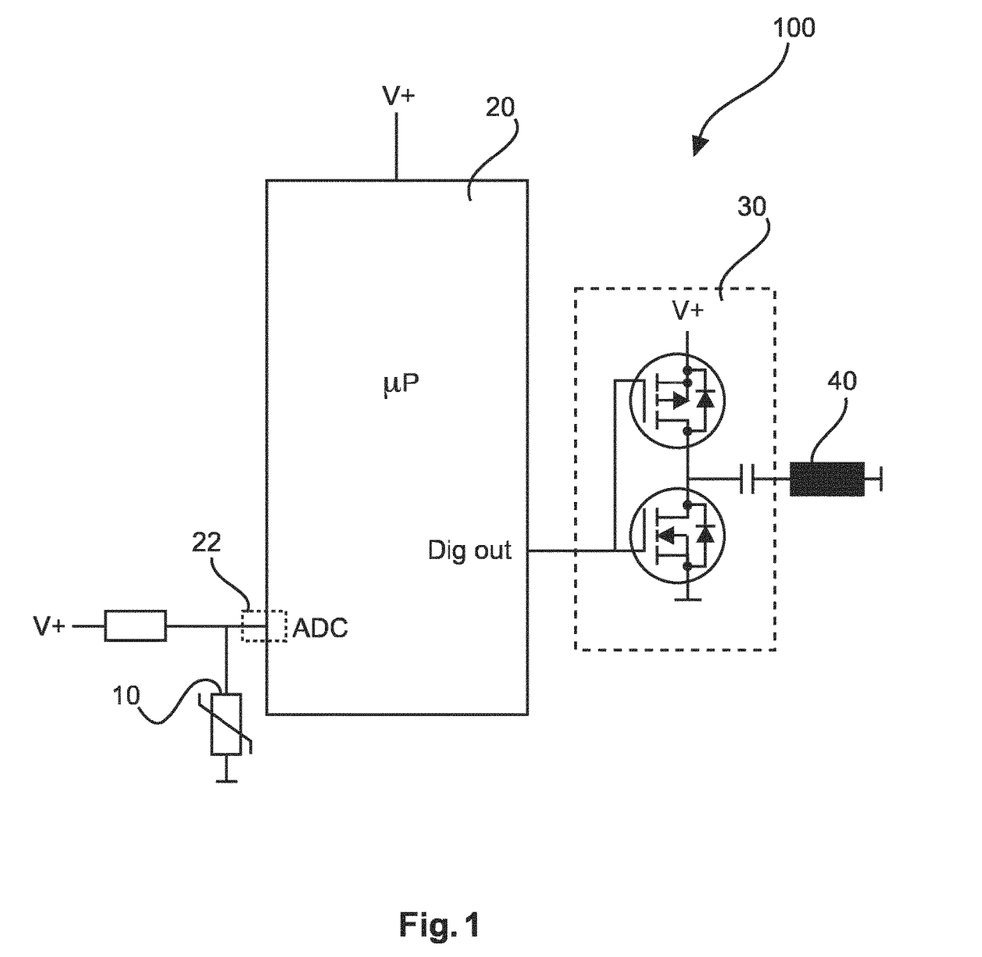
FIG. 1 shows a schematic diagram of a system for controlling a temperature according to an exemplary embodiment of the present invention.

The illustration in the drawings is purely schematical and does not intend to provide scaling relations or size information. In different drawings or figures, similar or identical elements are provided with the same reference numerals. Generally, identical parts, units, entities or steps are provided with the same reference symbols in the description. FIG. 1 shows a schematic diagram of a system for controlling a temperature according to an exemplary embodiment of the present invention.

A system 100 for controlling a temperature may comprise a temperature sensor module 10, a microcontroller module 20, a coupling module 30, and a heating module 40.

The temperature sensor module 10 may be configured to measure a temperature value.

The microcontroller module 20 may be coupled to the temperature sensor module 10 and may be configured to generate AC heating pulse signals by separate sequential code steps based on the measured temperature value.

The coupling module 30 may be coupled to the microcontroller module 20 and may be configured to transform the generated AC heating pulse signals into transformed AC heating pulse signals using a transfer function which is substantially zero for DC signal components.

The microcontroller module 30 may be configured to control the amplitudes of the generated AC heating pulse signals using a digital-to-analogue converter. The heating module 40 may be coupled to the coupling module 30 and may be configured to generate heat according to the transformed AC heating pulse signals.

A micro controller (or microprocessor, µP) used as the microcontroller module 20 may comprise an analog input 22 coupled to a temperature sensor used as the temperature sensor module 10 and a digital output capacitive used as the coupling module 30 may be coupled to a heater resistor used as the heating module 40. A software control loop may generate heating pulses which result in an AC current into the heater. The heater may comprise any dissipative component, e.g. a resistor, or a semiconductor etc. The AC coupling may be achieved via a capacitor or inductively via a transformer.

The system 100 for controlling a temperature may further comprise to a user-interface for setting the desired temperature and communicating status/errors to the user.

To deliver sufficient output current, a power driver comprising two switching FET's may be added. The temperature sensor may be a NTC, PTC, thermo-couple, semiconductor or any other temperature dependent device. The total circuit may be operating on one single supply voltage, e.g. 5 Volt.

The control algorithm inside the micro controller may take care of:
1. Voltage to temperature conversion of the temperature sensor signal
2. Generation of an error signal, being the difference between a desired temperature set-point and the actual temperature.
3. Loop filtering
4. Generation of heating pulses
5. Modifying the duty-cycle or the frequency of said heating pulses in response to the output of the loop filter.
6. Safety measures to prevent overheating on basis of e.g. power output during a time interval, temperature sensor out-of-range, temperature difference between two temperature sensors out of range, ADC failure by checking the absence of sample jitter or similar.

Advantageously, an occurring hardware failure of the switching FET's may increase the supply current, but will not generate dissipation in the heater.

Figure 2:
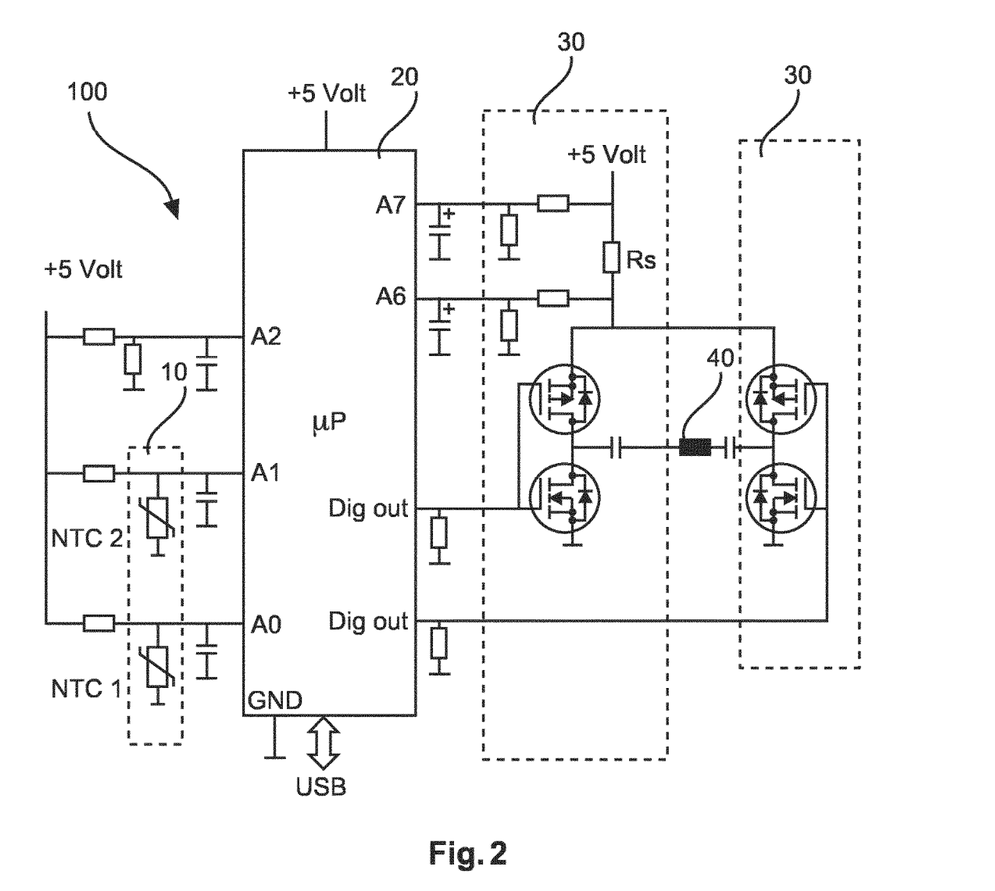
FIG. 2 shows a schematic diagram of a system for controlling a temperature according to a further exemplary embodiment of the present invention.

FIG. 2 shows a schematic diagram of a system for controlling a temperature according to a further exemplary embodiment of the present invention.

Contrary to FIG. 1, in FIG. 2, a further exemplary embodiment of the present invention is shown. The driver circuitry may be extended to an H-bridge. This may double the voltage and may increase the required impedance levels for achieving the same output power with a factor of four and consequentially a four times smaller capacitor, or four times slower heating pulses, which implies that a slower microprocessor may be required.

Two temperature sensors, Negative Temperature Coefficient Thermistors, NTC, e.g. NTC1 and NTC2 may be applied for safety (redundancy) reasons and may be set to determine the heat-flux from the heater into the skin. ADC input A2 may be utilized for normalization of the temperature measurement. The normalization may allow compensating for any supply voltage fluctuations. The analogue input signals are first voltage-divided in order to fit well within the analogue input range of the on-chip ADC.

The dissipated power in the heater is calculated from the supply voltage and the average voltage-drop across sensing resistor Rs. Obviously; said power must be corrected for the power loss in the switching field-effect transistor's, FET.

Figure 3:
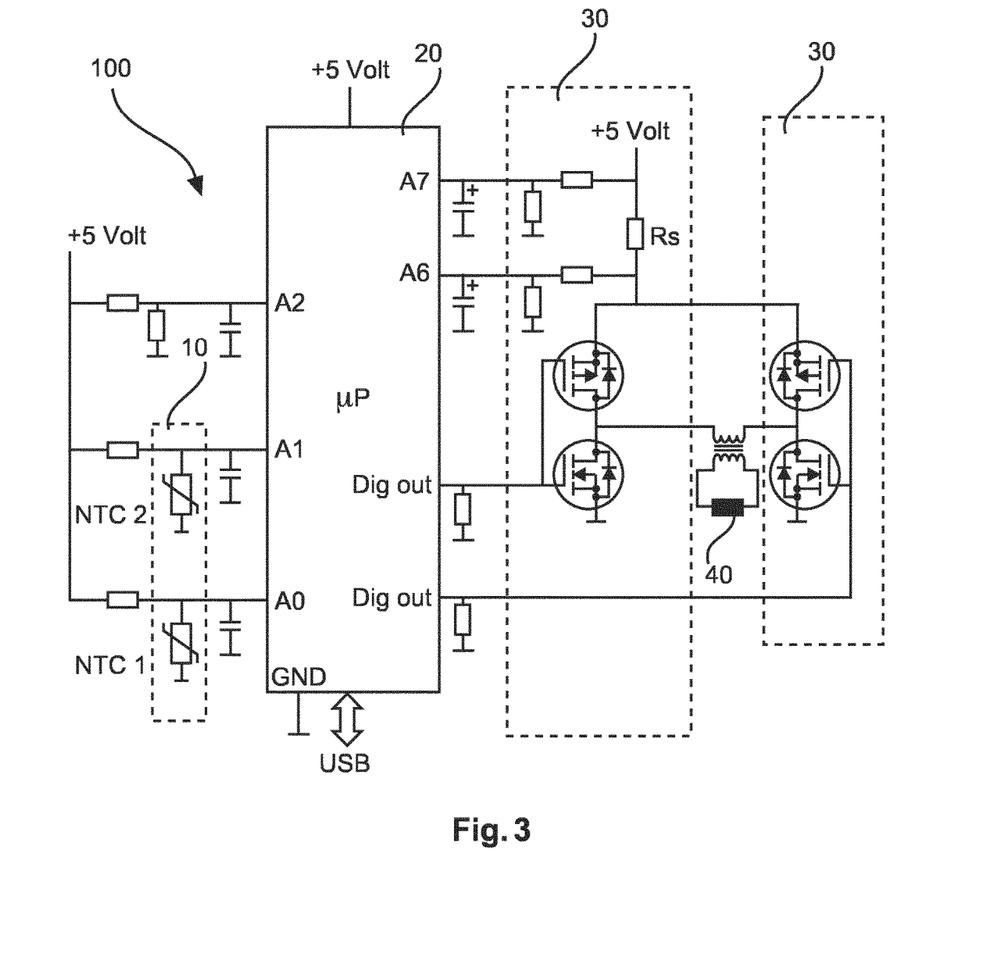
FIG. 3 shows a schematic diagram of a system for controlling a temperature according to a further exemplary embodiment of the present invention.

FIG. 3 shows a schematic diagram of a system for controlling a temperature according to a further exemplary embodiment of the present invention.

Contrary to FIG. 1 and to FIG. 2, a further exemplary embodiment of the present invention in FIG. 3 shows the heater inductively coupled to the driver circuitry. The transformer may be part of the sensor head or be part of a disposable plaster comprising the sensor spot in order to enable e.g. the positioning of the heater closely to the skin to avoid thermal gradients.

Figure 4:
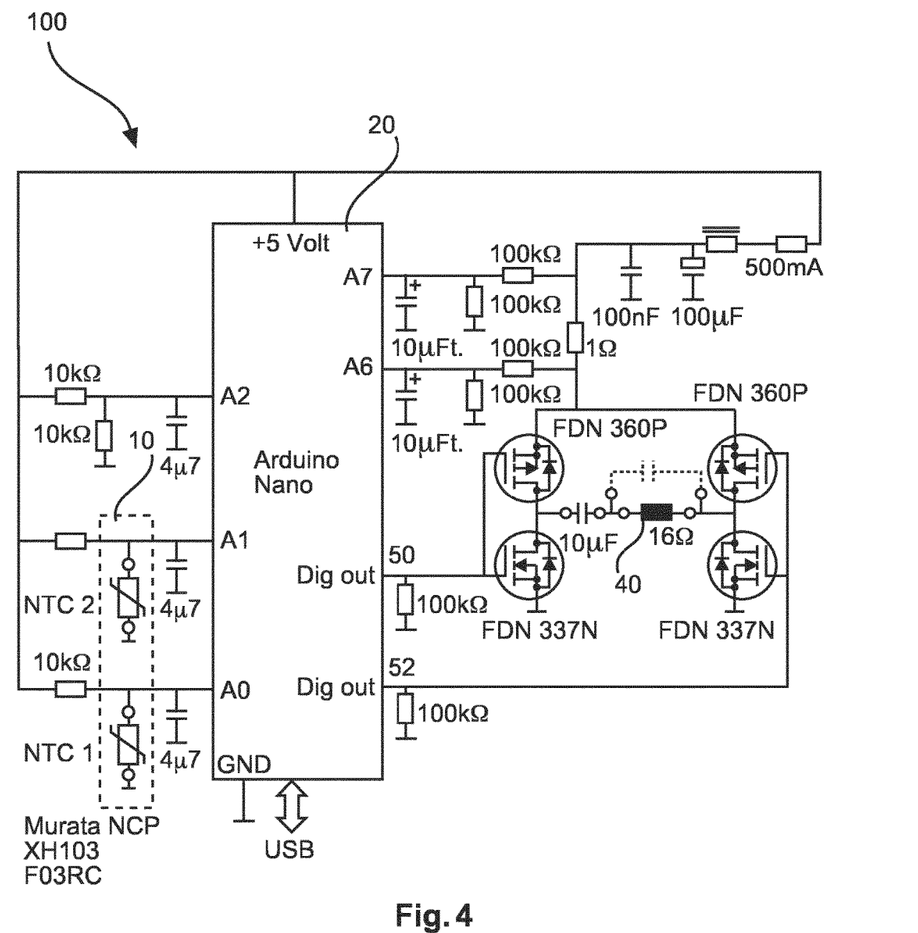
FIG. 4 shows a schematic diagram of a system for controlling a temperature according to a further exemplary embodiment of the present invention.

FIG. 4 shows a schematic diagram of a system for controlling a temperature according to a further exemplary embodiment of the present invention.

According to the exemplary embodiment of the present invention as shown in FIG. 4, the two NTC's and the heater are located in the probe-head, which is connected via an approximately 1 meter long cable, for instance 1 m+/−0.2 m, to the electronics. To avoid any Electromagnetic compatibility, EMC, issues, proper de-coupling may be added. Both branches of the H-bridge may be controlled in anti-phase in such a way that the resulting heater voltage shows as depicted in the next Figure.

Figure 5:
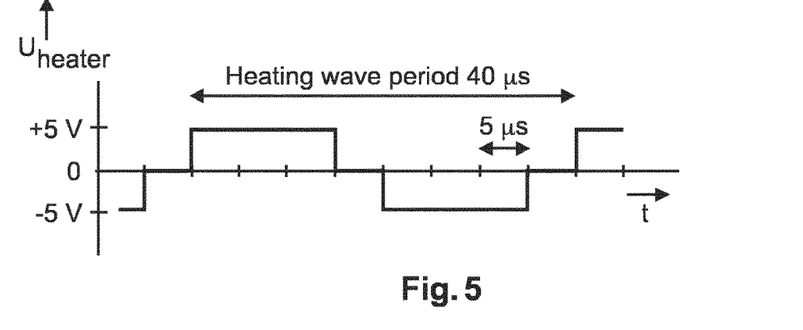
FIG. 5 shows a voltage versus time diagram for explaining the present invention.

FIG. 5 shows a voltage versus time diagram for explaining the present invention. In FIG. 5, a heating wave of a period of 40 µs is shown. The 0 Volt stairs are dictated by the practical limitation of the software library. This limits the maximum attainable power. The amplitude of the AC signal is 5 Volts.

Figure 6:
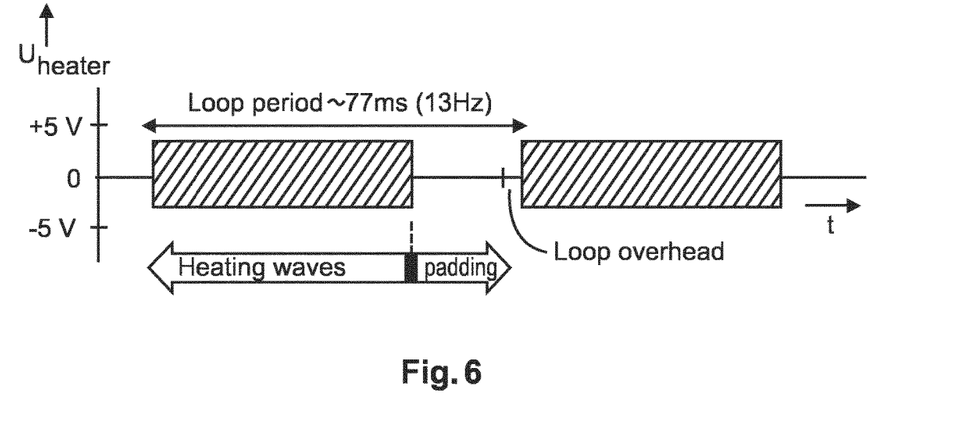
FIG. 6 shows a voltage versus time diagram for explaining the present invention.

FIG. 6 shows a voltage versus time diagram for explaining the present invention. In FIG. 6, continuously repeated cycles through a loop are shown, where a fixed 95% of the loop period is reserved for heating waves. The actual number of heating waves may be adapted to the needs of the temperature controller. In order to keep the total number of waves constant, zero-energy 'padding waves' are added. In FIG. 6, a heating wave of a period of 77 ms is shown, corresponding to 13 Hz.

Figure 7:
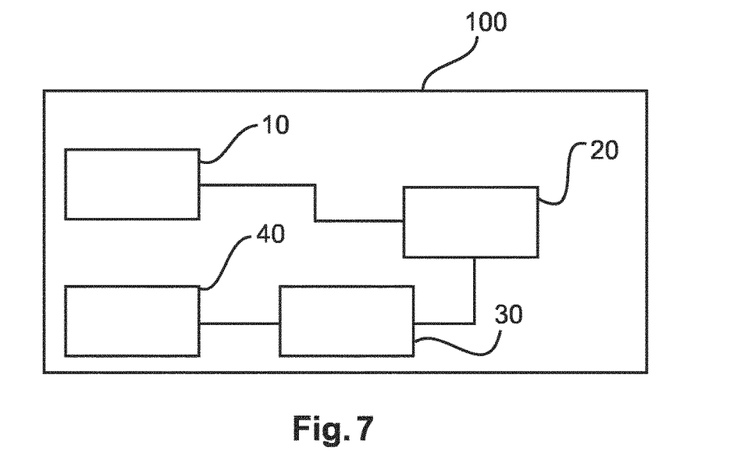
FIG. 7 shows a schematic diagram of a system for controlling a temperature according to a further exemplary embodiment of the present invention.

FIG. 7 shows a schematic diagram of a system for controlling a temperature according to a further exemplary embodiment of the present invention.

A system 100 for controlling a temperature may comprise a temperature sensor module 10, a microcontroller module 20, a coupling module 30, and a heating module 40.

The temperature sensor module 10 may be configured to measure a temperature value.

The microcontroller module 20 may be coupled to the temperature sensor module 10 and may be configured to generate AC heating pulse signals based on the measured temperature value.

The microcontroller module 20 may be coupled to additional communication means (not drawn) for control and monitoring.

The coupling module 30 may be coupled to the microcontroller module 20 and may be configured to transform the generated AC heating pulse signals into transformed AC heating pulse signals using a transfer function which is substantially zero for DC signal components.

The heating module 40 may be coupled to the coupling module 30 and may be configured to generate heat according to the transformed AC heating pulse signals.

The coupling module 30 may be configured to provide a higher order high-pass filter or band-pass filter. In this way the output power is more strongly decreased when the period of the heating waves deviates (for instance the period of the heating wave may increase or decrease) from its intended value, which may happen due to software interrupts, software flaws or changes in processor clock frequency or execution time. The higher order high-pass filter or band-pass filter advantageously provides an even more robust and safe operation of the system.

Possible parameters used for the electrical components of the system for controlling a temperature and possible parameters for current, frequencies and voltages are the following:

R heater of 16.5 Ohm, $U_{peak}$ of 4.4 V, $I_{peak}$ of 0.27 A, heating wave duty cycle of 0.75, control-loop duty cycle of 0.95, RMS heating power of 836 mW, $T_{instru}$ (time period used for instructions) of 5 µs, number of instructions per heating wave of 8, a heating wave period of 8 times 5µs, e.g. 40 µs, corresponding to 25 kHz, $\tau=4*T_{HWP}$ of 160 µs, wherein $\tau$ is a characteristic time period, and a coupling capacitor of 10 µF.

At maximum (95% duty cycle) 836 mW heating power can be generated into a 16.5Ω heater. The time constant of the AC coupling is chosen to be 4 times the loop period; hence the required coupling capacitor is 10 µF. To safe-guard shortage of the coupling capacitor, a series arrangement of at least two 20 µF capacitors can be applied.

Figure 8:
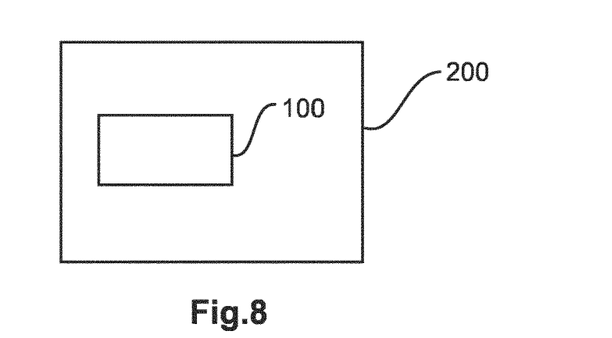
FIG. 8 shows a schematic diagram of a medical system according to an exemplary embodiment of the present invention.

FIG. 8 shows a schematic diagram of a medical system according to an exemplary embodiment of the present invention.

A medical system 200 may comprise a system 100 for controlling a temperature. The medical system 200 may be a system for measuring $CO_2$ blood gas level or an arterial blood gas analyser. The medical system 200 may be wearable, preferably cable-less.

Figure 9:
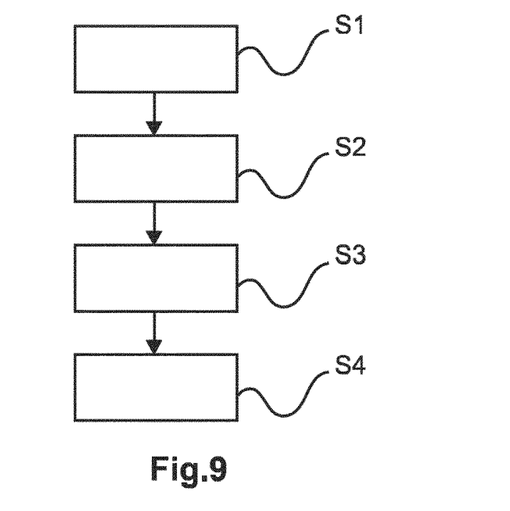
FIG. 9 shows a schematic diagram of a flowchart of a method for controlling a temperature according to an exemplary embodiment of the present invention.

FIG. 9 shows a schematic diagram of a flowchart of a method for controlling a temperature according to an exemplary embodiment of the present invention.

The method for controlling a temperature may comprise the following steps of:

As a first step of the method, measuring S1 a temperature value by means of a temperature sensor module 10 may be performed.

As a second step of the method, generating S2 AC heating pulse signals by separate sequential code steps based on the measured temperature value by means of a microcontroller module 20.

As a third step of the method, transforming S3 the generated AC heating pulse signals into transformed AC heating pulse signals using a transfer function which is substantially zero for DC signal components by means of a coupling module 30.

As a fourth step of the method, generating S4 heat according to the transformed AC heating pulse signals by means of a heating module 40.

The steps of the method may be iteratively or recursively repeated.

It has to be noted that embodiments of the present invention are described with reference to different subject-matters. In particular, some embodiments are described with reference to method type claims, whereas other embodiments are described with reference to the device type claims. However, a person skilled in the art will gather from the above and the foregoing description that, unless otherwise notified, in addition to any combination of features belonging to one type of the subject-matter also any combination between features relating to different subject-matters is considered to be disclosed within this application. However, all features can be combined providing synergetic effects that are more than the simple summation of these features.

While the present invention has been illustrated and described in detail in the drawings and the foregoing description, such illustration and description are to be considered illustrative or exemplary and not restrictive; the present invention is not limited to the disclosed embodiments.

Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. Any reference signs in the claims should not be construed as limiting the scope.

The invention claimed is:

1. A system for controlling a temperature for skin heating, the system comprising:
    a temperature sensor module, which is configured to measure a temperature value of the skin to be heated;
    a microcontroller module, which is coupled to the temperature sensor module and which is configured to compare a desired temperature and the measured temperature value and to generate AC heating pulse signals by separate sequential code steps based on the temperature comparison, wherein every single AC heating pulse signal requires the execution of distinct code steps by the microcontroller module;
    a coupling module, which is coupled to the microcontroller module and which is configured to transform the generated AC heating pulse signals into transformed AC heating pulse signals using a transfer function which is substantially zero for DC signal components, wherein the transfer function is lower than 0.1 for the DC signal components;
    a heating module, which is coupled to the coupling module and which is configured to generate heat according to the transformed AC heating pulse signals in the form of heating pulses of a time interval between 1 µs and 500 ms; and
    a memory module, which is coupled to or included in the microcontroller module and which is configured to store the code steps used by the microcontroller module.

2. The system according to claim 1, wherein the microcontroller module is a multi-core or a single-core processor and is configured to be operated in sequential processing.

3. The system according to claim 1, wherein the coupling module is configured to attenuate the DC signal components to a value of less than 4% of an input DC signal component, to a value of less than 2% of an input DC signal component, or to a value of less than 0.5% of an input DC signal component.

4. The system according to claim 1, wherein the microcontroller module is configured to generate the AC heating pulse signals based on the temperature comparison using a duty-cycle modulation.

5. The system according to claim 4, wherein the microcontroller module is configured to
    calculate an amount of requested thermal energy based on the temperature comparison, and
    control the duty cycle of the generated AC heating pulses based on the calculated amount of requested thermal energy.

6. The system according to claim 1, wherein the microcontroller module is configured to generate a period time of the AC heating pulse signals based on the temperature comparison using a frequency modulation.

7. The system according to claim 6, wherein the microcontroller module is configured to:
    calculate an amount of requested thermal energy based on the temperature comparison, and
    control the period time of the generated AC heating pulses based on the calculated amount of requested thermal energy.

8. The system according to claim 7, wherein the microcontroller module is configured to control a frequency or an amplitude of the generated AC heating pulse signals.

9. The system according to claim 1, wherein the heating module is a resistive element or a resistor.

10. The system according to claim 1, wherein the coupling module is a capacitor or an inductor or a transformer.

11. The system according to claim 1, wherein the coupling module comprises a driver circuit.

12. The system according to claim 1, wherein the microcontroller module comprises an analogue input, to which the temperature sensor module is coupled to.

13. A medical system comprising a system according to claim 1.

14. The system according to claim 1, wherein the time interval of the heating pulses is between between 2 µs and 30 ms.

15. A method for controlling a temperature for skin heating, the method comprising the steps of:
    measuring a temperature value of the skin to be heated by means of a temperature sensor module;
    comparing a desired temperature and the measured temperature value and generating AC heating pulse signals by separate sequential code steps based on the temperature comparison by means of a microcontroller module, wherein every single AC heating pulse signal requires the execution of distinct code steps by the microcontroller module, and wherein the code steps are stored in a memory module which is coupled to or included in the microcontroller module;
    transforming the generated AC heating pulse signals into transformed AC heating pulse signals using a transfer function which is substantially zero for DC signal components by means of a coupling module, wherein the transfer function is lower than 0.1 for the DC signal components; and generating heat according to the transformed AC heating pulse signals by means of a heating module in form of heating pulses of a time interval between 1 μs and 500 ms.

16. The system according to claim 14, wherein the time interval of the heating pulses is between 5 μs and 100 μs.

17. The method according to claim 15, wherein the time interval of the heating pulses is between between 2 μs and 30 ms.

18. The method according to claim 17, wherein the time interval of the heating pulses is between 5 μs and 100 μs.

* * * * *